United States Patent
Anto et al.

(10) Patent No.: US 10,969,373 B2
(45) Date of Patent: Apr. 6, 2021

(54) SYSTEM AND METHOD FOR WIRELESS PORTABLE GAS DETECTING AND COMMUNICATION

(71) Applicant: HONEYWELL INTERNATIONAL INC., Morris Plains, NJ (US)

(72) Inventors: Agnel Anto, Morris Plains, NJ (US); Chetan Sheelavant, Morris Plains, NJ (US); Shine K. Hari, Morris Plains, NJ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 16/258,089

(22) Filed: Jan. 25, 2019

(65) Prior Publication Data

US 2019/0234924 A1    Aug. 1, 2019

(30) Foreign Application Priority Data

Jan. 29, 2018   (IN) .............................. 201811003258

(51) Int. Cl.
  *G08B 21/00*    (2006.01)
  *G01N 33/00*    (2006.01)

(52) U.S. Cl.
  CPC ..... *G01N 33/0063* (2013.01); *G01N 33/0022* (2013.01); *G01N 33/0031* (2013.01)

(58) Field of Classification Search
  CPC ........... G01N 33/0022; G01N 33/0031; G01N 33/0063
  USPC ......................................................... 340/632
  See application file for complete search history.

(56) References Cited

U.S. PATENT DOCUMENTS

| | | | |
|---|---|---|---|
| 2008/0182215 A1* | 7/2008 | Sid .......................... | B60K 28/10 431/18 |
| 2010/0156647 A1* | 6/2010 | Thorson .................. | G01N 31/22 340/632 |
| 2010/0201531 A1* | 8/2010 | Pakravan ................ | G08B 21/14 340/632 |
| 2011/0037599 A1* | 2/2011 | Johnson, Jr. ........... | H04W 16/18 340/632 |
| 2011/0161885 A1* | 6/2011 | Gonia ..................... | G08B 25/14 715/847 |
| 2013/0008787 A1* | 1/2013 | Mammoto .............. | G08B 17/10 204/407 |
| 2013/0278412 A1* | 10/2013 | Kelly ...................... | G08B 26/00 340/539.1 |

(Continued)

*Primary Examiner* — Mark S Rushing
(74) *Attorney, Agent, or Firm* — Alston & Bird LLP (57) ABSTRACT

Embodiments relate generally to methods and systems for sensing and communicating characteristics of a work environment. A communication system may comprise one or more of the following one or more low cost sensor unit (LCSU) configured to detect one or more characteristics of the environment; one or more portable gas detector configured to be carried by a worker in the work environment, and comprising at least one sensor element, a display, and a wireless communication module; and one or more mobile device to be carried by a worker in the work environment, and comprising a display and a wireless communication module, wherein at least one of the portable gas detector and the mobile device is configured to receive sensed data from the one or more low cost sensor unit, process the received sensed data, and display the received sensed data to the worker.

20 Claims, 3 Drawing Sheets

(56) References Cited

U.S. PATENT DOCUMENTS

| | | | |
|---|---|---|---|
| 2014/0349707 A1* | 11/2014 | Bang | H04Q 9/00 455/556.1 |
| 2015/0010438 A1 | 1/2015 | Heng et al. | |
| 2015/0302719 A1* | 10/2015 | Mroszczak | G08B 21/0446 340/539.12 |
| 2017/0023509 A1 | 1/2017 | Kim et al. | |
| 2017/0093105 A1 | 3/2017 | Belinksky et al. | |
| 2018/0231515 A1* | 8/2018 | Voumard | G08B 21/182 |

* cited by examiner

SYSTEM AND METHOD FOR WIRELESS PORTABLE GAS DETECTING AND COMMUNICATION

CROSS-REFERENCE TO RELATED APPLICATIONS

The present application claims priority to India Provisional Patent Application Serial No. 201811003258 filed Jan. 29, 2018 by Agnel Anto, et al. and entitled "System and Method for Wireless Portable Gas Detecting and Communication" which is incorporated herein by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

In hazardous work environments, workers may carry gas detectors with them as they work, to allow for detection of gas exposure. The gas detector may alert the user if exposure limits are reached while the user is wearing the gas detector. Gas detectors may comprise interfaces for communicating with the user, such as displays, lights, buzzers, and input buttons. Gas detectors may be configured with settings for alarms, exposure limits, display settings, light and buzzer settings, etc.

SUMMARY

In an embodiment, a communication system may comprise one or more of the following one or more low cost sensor unit (LCSU) configured to detect one or more characteristics of the environment; one or more portable gas detector configured to be carried by a worker in the work environment, and comprising at least one sensor element, a display, and a wireless communication module; and one or more mobile device to be carried by a worker in the work environment, and comprising a display and a wireless communication module, wherein at least one of the portable gas detector and the mobile device is configured to receive sensed data from the one or more low cost sensor unit, process the received sensed data, and display the received sensed data to the worker.

In an embodiment, a method of communicating sensed data may comprise detecting, by one or more low cost sensor unit, one or more characteristics of the environment; sensing, by one or more portable gas detector, one or more characteristics so the environment, wherein the one or more portable gas detector is carried by a worker and comprises at least one sensor element, a display, and a wireless communication module; receiving, by at least one of a portable gas detector and a mobile device, sensed data from the one or more low cost sensor unit; processing the received sensed data from the one or more low cost sensor unit and the one or more portable gas detector; and displaying the received sensed data to the worker.

In an embodiment, a portable gas detection system may comprise one or more low cost sensor unit configured to detect one or more characteristics of a work environment; communicate with at least one of a portable gas detector and a mobile device carried by a worker in the work environment; and send sensed data to at least one of the portable gas detector and the mobile device carried by a worker in the work environment, wherein at least one of the portable gas detector and the mobile device is configured to receive sensed data from the one or more low cost sensor unit, process the received sensed data, and display the received sensed data to the worker.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for increasing the detection capabilities of a gas detector device, for example, a portable gas detector that may be carried by a worker within a work environment. A portable gas detection system may comprise low cost sensor units (LCSUs), wearable display units, and/or portable gas detectors. A user of a wearable display unit and/or portable gas detector may select among different LCSUs to obtain current (or saved) target gas concentration readings. A wearable display unit and/or portable gas detector can also generate and display average data obtained from multiple LCSUs.

Typical portable gas detectors may have limitations for the number of sensors which may be included in the portable gas detector, based on the size, weight, and other capacities of the portable gas detector. Additionally, typical portable gas detectors may have (semi) permanently fixed gas sensors installed within the portable gas detector, which limit the gas detector to just those specific gases than can be detected by the specific sensors. This would mean a customer, or user, would need to buy multiple types of portable gas detectors to cover a wider range of target gases. The customer may have to buy multiple individual gas detectors based on the sensor requirements. This may add cost to the customer.

Embodiments of the disclosure include systems and methods for extending or increasing (virtually) the sensing capabilities of one or more portable gas detectors and/or other mobile or wearable devices. The virtual extension of a portable gas detector may not add to individual materials cost of the unit nor will it degrade the performance of existing portable gas detectors. The disclosed systems and methods may have improved utilization of software resources, time savings in terms of re-configuration of devices, and an improved user experience. A user may be able to access gas sensor readings without having the sensors physically in a device the user is carrying (e.g., portable gas detector, mobile device, wearable device).

Individual LCSUs with a low range wireless connectivity can function as virtual sensor array units, wherein the LCSUs may comprise one or more sensor elements and one or more wireless communication modules. The LCSUs can be automatically detected (and possibly automatically connected to) by portable gas detectors (or other mobile devices), where the portable gas detectors may comprise one or more wireless communication modules. The user can use a display of the portable gas detector (or other mobile devices) to select from the available and wirelessly connected LCSUs, which may be installed in the vicinity, to obtain a target gas concentration reading. The LCSUs may be different from typical fixed gas detectors in terms of cost, features, and form factor. The LCSUs may be easily carried and installed at strategic locations in the work environment by a user without having any formal training related to installation. In short, LCSUs are low cost, miniature portable units which can be carried by the user like personal equipment, but the data is accessed by multiple users.

In some embodiments, a portable gas detector (or other mobile device) may be configured to receive and analyze the sensed data from multiple LCSUs and display the analyzed data to the user via a display of the portable gas detector. In some additional embodiments, a user (or worker) could carry a mobile device and/or wearable display unit (which may or may not comprise sensors within the mobile device or wearable display unit) configured to wirelessly communicate with the LCSUs within range of the wearable display unit. Similar to the portable gas detector, the wearable display unit may be configured to receive and analyze the sensed data from multiple LCSUs and display the analyzed data to the user via a display of the wearable display unit. In some embodiments, the portable gas detector (and/or wearable display unit) may be configured to generate alarms and alerts based on the information received from the LCSUs, for example, when a target gas is over or under a certain threshold value.

Figure 1:
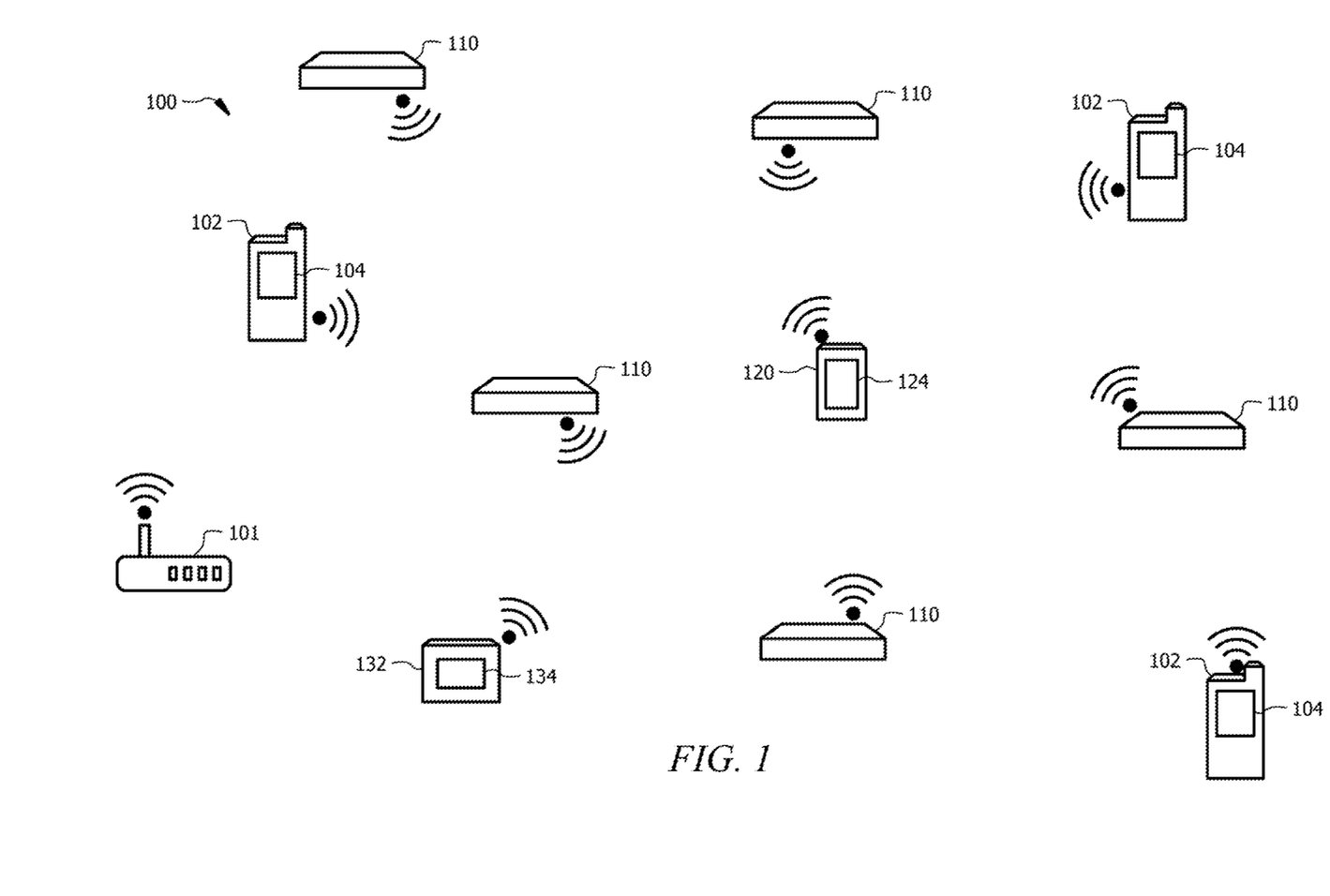
FIG. 1 illustrates a communication system according to an embodiment of the disclosure.

Referring now to FIG. 1, a communication system 100 is shown, where the system 100 may comprise a plurality of portable gas detectors 102 carried by users within a work environment. In other words, the communication system 100 may exist within a work environment. A portable gas detector 102 may comprise a display 104 (which may also be called a user interface, and may include other elements of a user interface, such as buttons, lights, indicators, etc.) configured to allow a user to interact with the portable gas detector 102. The portable gas detector(s) 102 may comprise a memory, processor, and/or communication modules configured to receive sensed data, send sensed data, store sensed data, process (analyzed) sensed data, etc. In some embodiments, the gas detector(s) 102 may comprise at least one sensor element configured to detect a characteristic of the surrounding environment (e.g., gas, temperature, humidity, pressure, etc.).

The communication system 100 may also comprise a plurality of LCSUs 110 (or another similar type of sensor unit) that may be placed in strategic locations throughout the work environment. In some embodiments, the LCSUs 110 may be semi-permanently placed in a location or may be in a fixed location (where the LCSU 110 may be moved around to different areas of the work environment, but may be placed in a location for an extended period of time, and may not typically be carried by a worker in the same way as the portable gas detector 102, mobile device 120 and/or wearable device 130). The LCSUs 110 may be located based on expected gas detection, known potential hazards, or other characteristics of the work environment. The LCSUs 110 may comprise a memory, a processor, and/or communication modules configured to receive sensed data, send sensed data, store sensed data, process (analyze) sensed data, etc. In some embodiments, the LCSUs 110 may comprise at least one sensor element configured to detect a characteristic of the surrounding environment (e.g., gas, temperature, humidity, pressure, etc.).

In some embodiments, the communication system 100 may be facilitated by a wireless router 101 or other wireless communication system. The wireless means of communication may comprise Bluetooth (BLE), Wi-Fi, Li-Fi, LTE, mesh-network, etc. The wireless router 101 may facilitate communication between the portable gas detectors 102, LCSUs 110, and any other computers, monitors, central stations, etc., that may be located within the work environment.

As described above, the LCSUs may be equipped with one or more gas sensors (or other sensor elements configured to detect environmental conditions). In some embodiments, the LCSUs 110 may be equipped with one or more gas sensors that are not included in the portable gas detector(s) 102, so that the data collected by the LCSUs 110 may supplement the data collected by the portable gas detectors 102. For example, the LCSUs 110 may comprise a first gas detector configured to detect a first gas, and the portable gas detector(s) 102 may comprise a second gas detector configured to detect a second gas that is different from the first gas.

In some embodiments, a portable gas detector 102 may be configured to receive sensed data from one or more LCSU 110 via a wireless connection. The portable gas detector 102 may be configured to analyze the data received from the LCSUs 110, and optionally generate a display screen that includes the analyzed data from the LCSUs 110. In some embodiments, the portable gas detector 102 may display a list of the current LCSUs 110 that are connected to the portable gas detector 102 (or optionally have at least at one time been connected to the portable gas detector 102). A user may be able to display the sensed data from a specific LSCU 110 using the display and/or list of the LCSUs. In another embodiment, a user may be able to display a summary of all of the sensed data collected by the gas detector 102, from the sensors within the gas detector 102 and/or the LSCUs 110.

In some embodiments, the communication system 100 may also comprise one or more mobile devices 120 with display 124 configured to wirelessly communicate with other devices within the communication system 100, as described above. In some embodiments, the communication system 100 may also comprise one or more wearable device 130 with display 134 configured to wirelessly communicate with other devices within the communication system 100, as described above.

A typical portable gas detector 102 may be capable of holding up to five sensor elements (as an example), where any more sensor elements may cause the gas detector to be too large and/or heavy to be feasibly portable. The LSCUs 110 could be larger or heavier than the portable gas detector 102, since they will not be carried by the user while working, and may be placed in fixed locations within the work environment, but may be relocated to another location within the work environment. The LSCUs 110 may be easily moved to another location, but may also not be regularly carried by a worker.

In some embodiments, the sensor elements that are located within the LCSUs 110 may comprise duplicate sensors (i.e., sensors configured to detect the same target gas or other environment characteristic) to other sensors in the same LCSU 110, other LCSUs 110, and/or the portable gas detectors 102 within the communication system 100. The duplication of sensor elements may provide a safety backup measure in the event that one of the sensor elements fails. The duplication and safety backup may be useful for sensors configured to detect critical data, such as oxygen sensors, particularly harmful gas sensors, etc.

Figure 2A:
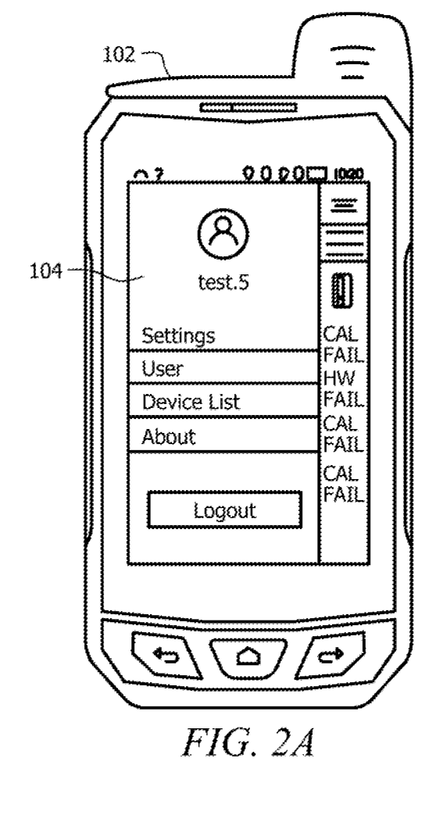
FIG. 2A illustrates a menu display of a portable gas detector according to an embodiment of the disclosure.
Figure 2B:
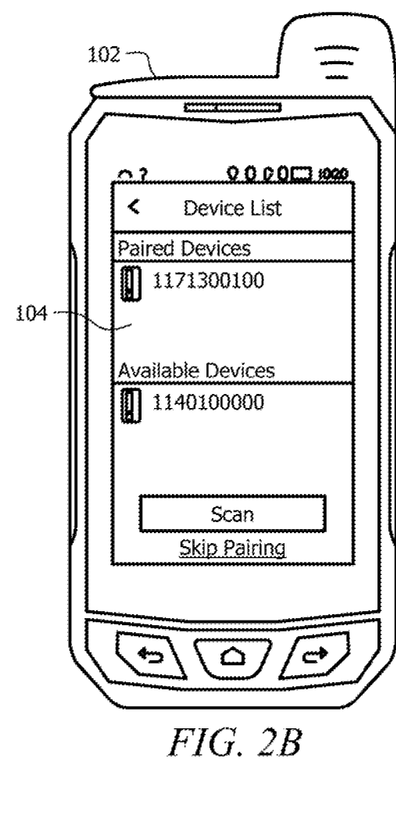
FIG. 2B a device list display of a portable gas detector according to an embodiment of the disclosure.
Figure 2C:
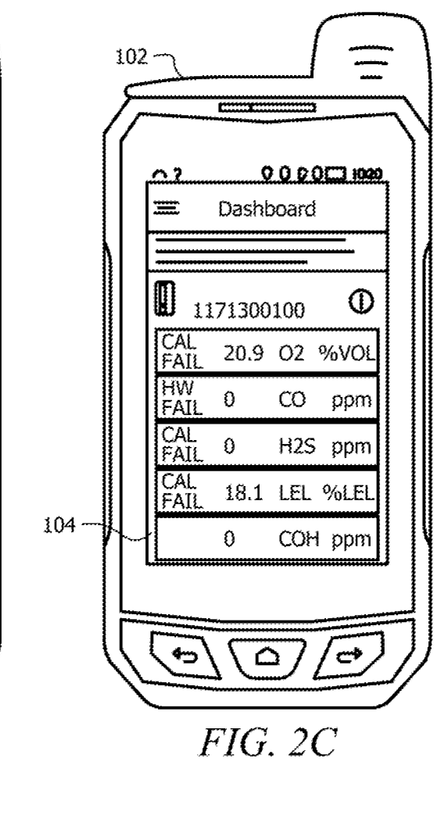
FIG. 2C a dashboard display of a portable gas detector according to an embodiment of the disclosure.

Referring to FIGS. 2A-2C, exemplary displays 104 of the portable gas detector 102 are shown. FIG. 2A illustrates an exemplary menu display. FIG. 2B illustrates an exemplary device list display (e.g., a list of LCSUs connected to the gas detector 102). FIG. 2C illustrates an exemplary dashboard display comprising sensed data information (where the sensed data may be detected by the gas detector 102 and/or LCSUs in communication with the gas detector 102).

Figure 3:
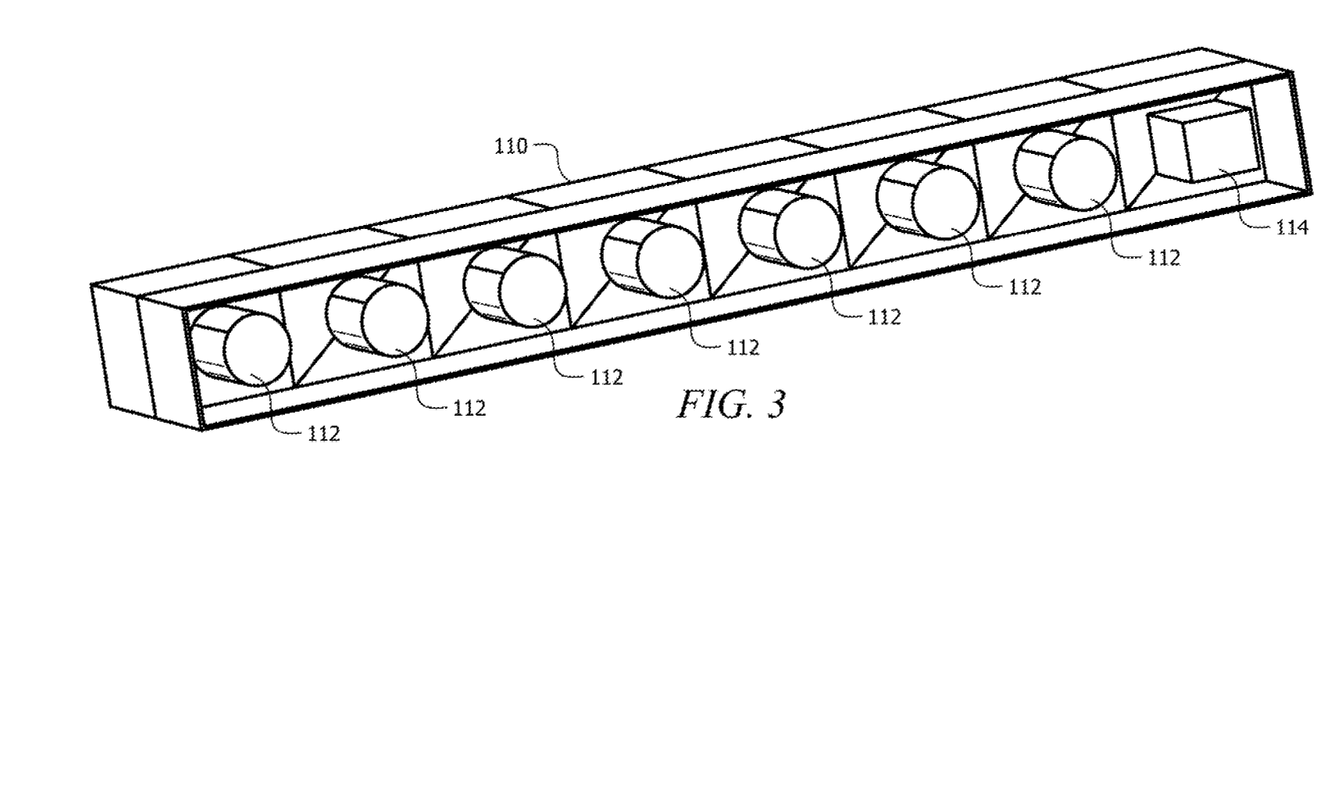
FIG. 3 illustrates a low cost sensor unit according to an embodiment of the disclosure.

Referring to FIG. 3, an exemplary LCSU 110 is shown, wherein the LSCU 110 may comprise one or more sensor elements 112 configured to detect a target gas (and/or another environmental characteristic). In some embodiments, the LCSU 110 may comprise one or more pumps configured to direct sample gas toward (and/or away from) the sensor elements 112. In some embodiments, the sensor elements 112 may be replaceable and/or interchangeable, such that the LSCU 110 may be configured based on the needs of the user and the work environment. In some embodiments, the LCSU 110 may comprise an electronics unit 114 configured to receive data from the one or more sensor elements 112 and communicate the received data (possibly to a portable gas detector). In some embodiments, the electronics unit 114 of the LCSU 110 may comprise a signal conditional circuit (SCC) and/or one or more wireless communication modules. In some embodiments, the LCSU 110 may be compact and easy to place at a strategic location within a work environment.

In an embodiment of the disclosure, a communication system may comprise one or more of the following: one or more low cost sensor unit (LCSU) configured to detect one or more characteristics of the environment; one or more portable gas detector configured to be carried by a worker in the work environment, and comprising at least one sensor element, a display, and a wireless communication module; one or more mobile device to be carried by a worker in the work environment, and comprising a display and a wireless communication module; one or more wearable device to be worn (and therefore carried) by a worker in the work environment, and comprising a display and a wireless communication module, wherein at least one of the portable gas detector, mobile device, and/or wearable device is configured to receive sensed data from the one or more LCSU, process the received sensed data, and display the received sensed data to the worker.

Having described various devices and methods herein, exemplary embodiments or aspects can include, but are not limited to:

In a first embodiment, a communication system may comprise one or more of the following one or more low cost sensor unit (LCSU) configured to detect one or more characteristics of the environment; one or more portable gas detector configured to be carried by a worker in the work environment, and comprising at least one sensor element, a display, and a wireless communication module; and one or more mobile device to be carried by a worker in the work environment, and comprising a display and a wireless communication module, wherein at least one of the portable gas detector and the mobile device is configured to receive sensed data from the one or more low cost sensor unit, process the received sensed data, and display the received sensed data to the worker.

A second embodiment can include the communication system of the first embodiment, wherein the one or more mobile device comprises one or more wearable device configured to be worn by a worker in the work environment.

A third embodiment can include the communication system of the first or second embodiments, wherein the one or more mobile device comprises a smartphone carried by the worker.

A fourth embodiment can include the communication system of any of the first through third embodiments, wherein the one or more low cost sensor unit comprises a plurality of gas sensors configured to detect a plurality of gases.

A fifth embodiment can include the communication system of the fourth embodiment, wherein the plurality of sensor elements comprise replaceable or interchangeable sensor elements.

A sixth embodiment can include the communication system of the fourth or fifth embodiments, wherein the plurality of sensor elements comprise at least two sensors configured to detect the same target gas.

A seventh embodiment can include the communication system of any of the fourth through sixth embodiments, wherein the one or more low cost sensor unit comprises a first gas sensor configured to detect a first gas, and wherein the one or more portable gas detector comprises a second gas sensor configured to detect a second gas that is different from the first gas.

An eighth embodiment can include the communication system of any of the first through seventh embodiments, wherein the one or more low cost sensor unit comprises an electronics unit configured to communicate with one or more sensors and configured to communicate sensed data from the one or more sensors to at least one of the portable gas detector and the mobile device.

A ninth embodiment can include the communication system of the eighth embodiments, wherein the electronics unit comprises a wireless communication module.

In a tenth embodiment, a method of communicating sensed data may comprise detecting, by one or more low cost sensor unit, one or more characteristics of the environment; sensing, by one or more portable gas detector, one or more characteristics so the environment, wherein the one or more portable gas detector is carried by a worker and comprises at least one sensor element, a display, and a wireless communication module; receiving, by at least one of a portable gas detector and a mobile device, sensed data from the one or more low cost sensor unit; processing the received sensed data from the one or more low cost sensor unit and the one or more portable gas detector; and displaying the received sensed data to the worker.

An eleventh embodiment can include the method of the tenth embodiment, wherein displaying the received sensed data to the worker comprises displaying the received sensed data on the portable gas detector.

A twelfth embodiment can include the method of any of the tenth through eleventh embodiments, wherein displaying the received sensed data to the worker comprises displaying the received sensed data on mobile device.

A thirteenth embodiment can include the method of the twelfth embodiment, wherein the one or more mobile device comprises one or more wearable device configured to be worn by a worker in the work environment.

A fourteenth embodiment can include the method of the twelfth or thirteenth embodiments, wherein the one or more mobile device comprises a smartphone carried by the worker.

A fifteenth embodiment can include the method of any of the tenth through fourteenth embodiments, further comprising detecting a first gas via a first gas sensor of the one or more low cost sensor unit; and detecting a second gas via a second gas sensor of the one or more portable gas detector, wherein the second gas is different from the first gas.

In a sixteenth embodiment, a portable gas detection system may comprise one or more low cost sensor unit configured to detect one or more characteristics of a work environment; communicate with at least one of a portable gas detector and a mobile device carried by a worker in the work environment; and send sensed data to at least one of the portable gas detector and the mobile device carried by a worker in the work environment, wherein at least one of the portable gas detector and the mobile device is configured to receive sensed data from the one or more low cost sensor unit, process the received sensed data, and display the received sensed data to the worker.

A seventeenth embodiment can include the portable gas detection system of the sixteenth embodiment, further comprising one or more portable gas detector configured to be carried by a worker in the work environment, and comprising at least one sensor element, a display, and a wireless communication module; and one or more mobile device to be carried by a worker in the work environment and comprising a display and a wireless communication module.

An eighteenth embodiment can include the portable gas detection system of the sixteenth or seventeenth embodiments, wherein the one or more low cost sensor unit comprises a first gas sensor configured to detect a first gas, and wherein the first gas is different from a second gas, wherein the second gas is detected by a second gas sensor of the one or more portable gas detector.

A nineteenth embodiment can include the portable gas detection system of any of the sixteenth through eighteenth embodiments, wherein the one or more low cost sensor unit comprises a plurality of gas sensors configured to detect a plurality of gases.

A twentieth embodiment can include the portable gas detection system of any of the sixteenth through nineteenth embodiments, wherein the one or more low cost sensor unit comprises an electronics unit configured to communicate with one or more sensors and configured to communicate sensed data from the one or more sensors to at least one of the portable gas detector and the mobile device.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A communication system comprising:
   one or more low cost sensor unit (LCSU) configured to detect one or more characteristics of a work environment;
   one or more portable gas detector configured to be carried by a worker in the work environment, and comprising at least one sensor element, a display, and a wireless communication module, wherein the one or more portable gas detector is further configured to determine one or more target gases;
   one or more mobile device to be carried by the worker in the work environment, and comprising a display and a wireless communication module;
   wherein at least one of the one or more portable gas detector and the one or more mobile device is configured to:
   establish a connection with the one or more low cost sensor unit via the wireless communication module;
   display the one or more low cost sensor unit on a user interface;
   receive a user input to select the one or more low cost sensor unit via the user interface, wherein, along with the determination of the one or more target gases, the selected one or more low cost sensor unit is adaptable to determine one or more supplementary target gases;
   receive sensed data from the one or more low cost sensor unit, process the received sensed data, and display the sensed data indicative of current or saved target gas concentration readings of the one or more low cost sensor unit when the sensed data indicates a level of the one or more target gases or a level of the one or more supplementary target gases above a threshold value;
   generate alarms when the sensed data indicates the level of the one or more target gases or the level of the one or more supplementary target gases is above the threshold value, and
   wherein upon generating the alarms, only low cost sensors are displayed that are in range and that have exceeded a threshold value, and receiving a user input to select one of the displayed low cost sensors in order to display specific gas levels.

2. The communication system of claim 1, wherein the one or more mobile device comprises one or more wearable device configured to be worn by the worker in the work environment.

3. The communication system of claim 1, wherein the one or more mobile device comprises a smartphone carried by the worker.

4. The communication system of claim 1, wherein the one or more low cost sensor unit comprises a plurality of gas sensors configured to detect a plurality of gases.

5. The communication system of claim 4, wherein the plurality of gas sensors comprise replaceable or interchangeable sensor elements.

6. The communication system of claim 4, wherein the plurality of gas sensors comprise at least two sensors configured to detect a same target gas.

7. The communication system of claim 1, wherein the one or more low cost sensor unit comprises a first gas sensor configured to detect a first gas, and wherein the one or more portable gas detector comprises a second gas sensor configured to detect a second gas that is different from the first gas.

8. The communication system of claim 1, wherein the one or more low cost sensor unit comprises an electronics unit configured to communicate with one or more sensors and configured to communicate the sensed data from the one or more sensors to at least one of the one or more portable gas detector and the one or more mobile device.

9. The communication system of claim 8, wherein the electronics unit comprises a wireless communication module.

10. A method of communicating sensed data comprising:
   detecting, by one or more low cost sensor unit, one or more characteristics of a work environment;
   sensing, by one or more portable gas detector, one or more target gases, and one or more characteristics of the work environment, wherein the one or more portable gas detector is carried by a worker and comprises at least one sensor element, a display, and a wireless communication module;
   establishing a connection with the one or more portable gas detector by the one or more low cost sensor unit;
   displaying the one or more low cost sensor unit on a user interface of the one or more portable gas detector;
   selecting one or more low cost sensor unit via the user interface;
   determining, along with the sensing of the one or more target gases via the one or more portable gas detector, one or more supplementary target gases based on the one or more low cost sensor unit;
   receiving, by at least one of the one or more portable gas detector and one or more mobile device, sensed data from the one or more low cost sensor unit;
   processing the sensed data from the one or more low cost sensor unit and the one or more portable gas detector; and
   displaying the sensed data indicative of current or saved target gas concentration readings of the one or more low cost sensor unit and the one or more portable gas detector to the worker when the sensed data indicates a level of the one or more target gases or a level of the one or more supplementary target gases above a threshold value;

generating alarms when the sensed data indicates the level of the one or more target gases or the level of the one or more supplementary target gases is above the threshold value; and wherein upon generating the alarms, only low cost sensors are displayed that are in range and that have exceeded a threshold value, and receiving a user input to select one of the displayed low cost sensors in order to display specific gas levels.

11. The method of claim 10, wherein displaying the sensed data to the worker comprises displaying the sensed data on the one or more portable gas detector.

12. The method of claim 10, wherein displaying the sensed data to the worker comprises displaying the sensed data on the one or more mobile device.

13. The method of claim 12, wherein the one or more mobile device comprises one or more wearable device configured to be worn by the worker in the work environment.

14. The method of claim 12, wherein the one or more mobile device comprises a smartphone carried by the worker.

15. The method of claim 10, further comprising: detecting a first gas via a first gas sensor of the one or more low cost sensor unit; and detecting a second gas via a second gas sensor of the one or more portable gas detector, wherein the second gas is different from the first gas.

16. A portable gas detection system comprising:
one or more low cost sensor unit configured to:
  detect one or more characteristics of a work environment;
  communicate with at least one of a portable gas detector and a mobile device carried by a worker in the work environment; and
  send sensed data to at least one of the portable gas detector and the mobile device carried by the worker in the work environment,
wherein at least one of the portable gas detector and the mobile device is configured to:
  determine one or more target gases,
  establish a connection with the one or more low cost sensor unit via a wireless communication module;
  display the one or more low cost sensor unit on a user interface;
  receive a user input, via the user interface, to select one or more low cost sensor unit;
  receive, along with determination of the one or more target gases, sensed data from the one or more low cost sensor unit, process the sensed data, and display the sensed data indicative of current or saved target gas concentration readings of the one or more low cost sensor unit to the worker, when the sensed data indicates a level of the one or more target gases is above a threshold value;
  generate alarms when the sensed data indicates the level of the one or more target gases is above the threshold value; and
  wherein upon generating the alarms, only low cost sensors are displayed that are in range and that have exceeded a threshold value, and receiving a user input to select one of the displayed low cost sensors in order to display specific gas levels.

17. The portable gas detection system of claim 16, further comprising: one or more portable gas detector configured to be carried by the worker in the work environment, and comprising at least one sensor element, a display, and a wireless communication module; and one or more mobile device to be carried by the worker in the work environment and comprising a display and a wireless communication module.

18. The portable gas detection system of claim 17, wherein the one or more low cost sensor unit comprises a first gas sensor configured to detect a first gas, and wherein the first gas is different from a second gas, wherein the second gas is detected by a second gas sensor of the one or more portable gas detector.

19. The portable gas detection system of claim 16, wherein the one or more low cost sensor unit comprises a plurality of gas sensors configured to detect a plurality of gases.

20. The portable gas detection system of claim 16, wherein the one or more low cost sensor unit comprises an electronics unit configured to communicate with one or more sensors and configured to communicate the sensed data from the one or more sensors to at least one of the portable gas detector and the mobile device.

* * * * *